(12) United States Patent
Gonzalez et al.

(10) Patent No.: US 7,651,665 B2
(45) Date of Patent: Jan. 26, 2010

(54) MICROTRAY FOR HANDLING BIOSUBSTANCES

(75) Inventors: Jose M. Gonzalez, Guaynabo, PR (US); Carlos A. Martinez, Isabela, PR (US); Enrique C. Abreu, Mayaguez, PR (US); Roberto Rivera, Mayaguez, PR (US); John S. Dunfield, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1011 days.

(21) Appl. No.: 10/935,029

(22) Filed: Sep. 7, 2004

(65) Prior Publication Data
US 2006/0051250 A1    Mar. 9, 2006

(51) Int. Cl.
*B01L 3/00* (2006.01)
(52) U.S. Cl. .................. 422/100; 422/99; 422/102; 436/180
(58) Field of Classification Search .............. 422/100, 422/102
See application file for complete search history.

(56) References Cited

U.S. PATENT DOCUMENTS

| | | | |
|---|---|---|---|
| 4,262,711 A * | 4/1981 | Anderson | 141/238 |
| 4,753,775 A * | 6/1988 | Ebersole et al. | 422/81 |
| 5,985,214 A | 11/1999 | Stylli et al. | |
| 6,063,339 A | 5/2000 | Tisone et al. | |
| 6,264,891 B1 | 7/2001 | Heyneker | |
| 6,309,828 B1 | 10/2001 | Schleifer | |
| 6,350,618 B1 | 2/2002 | Borrelli et al. | |
| 6,485,690 B1 * | 11/2002 | Pfost et al. | 422/102 |
| 6,620,383 B1 | 9/2003 | Karg et al. | |
| 6,706,538 B1 | 3/2004 | Karg et al. | |
| 6,713,022 B1 | 3/2004 | Noolandi et al. | |
| 6,911,181 B1 * | 6/2005 | McNeil | 422/100 |
| 2002/0187478 A1 | 12/2002 | Childers | |
| 2003/0108451 A1 * | 6/2003 | Su et al. | 422/100 |
| 2003/0155034 A1 | 8/2003 | De Beukeleer et al. | |
| 2003/0161761 A1 | 8/2003 | Williams et al. | |
| 2005/0019775 A1 * | 1/2005 | Alderborn et al. | 435/6 |

FOREIGN PATENT DOCUMENTS

| | | |
|---|---|---|
| EP | 1 281 441 | 2/2003 |
| WO | WO 99/36176 | 7/1999 |
| WO | WO 00/24511 | 5/2000 |
| WO | WO 00/58735 | 10/2000 |
| WO | 00/66995 | * 11/2000 |
| WO | WO 00/66995 | 11/2000 |
| WO | WO 01/43876 | 6/2001 |
| WO | WO 02/18053 | 3/2002 |

(Continued)

OTHER PUBLICATIONS

"Footprint Dimensions for Microplates", Society for Biomolecular Screening, pp. 1-8, (Jan. 2004).

(Continued)

*Primary Examiner*—Jill Warden
*Assistant Examiner*—Dwan A Gerido

(57) ABSTRACT

A microtray for handling biosubstances comprises a fluid holding structure and a fluid ejection structure. The fluid holding structure includes an array of wells with each well configured to contain at least one biosubstance. The fluid ejection structure is in communication with the fluid holding structure and configured to dispense the at least one biosubstance onto a target media.

11 Claims, 6 Drawing Sheets

FOREIGN PATENT DOCUMENTS

| | | |
|---|---|---|
| WO | WO 03/068962 | 8/2003 |
| WO | WO 03/072258 | 9/2003 |
| WO | WO 03/074166 | 9/2003 |

OTHER PUBLICATIONS

"Height Dimensions for Microplates", Society for Biomolecular Screening, pp. 1-9, (Feb. 2004).

"Bottom Outside Flange Dimensions", Society for Biomolecular Screening, pp. 1-10, (Mar. 2004).

"Well Positions for Microplates", Society for Biomolecular Screening, pp. 1-13, (Apr. 2004).

"NimbleGen Custom Microarray Services", NimbleGen Systems, Inc., pp. 1-4, <www.nimblegen.com>.

"Packard BioChip Arrayer Non-Contact Microdispensing System", PerkinElmer Life Sciences, pp. 1-2, <www.perkinelmer.com/lifesciences>.

Kricka, Larry J., "Miniaturization of Analytical Systems", Clinical Chemistry—Kricka 44 (9): 2008, pp. 1-12, (1998), <www.clinchem.org/cgi>.

Gwynne, Peter and Heebner, Gary, "Technologies in DNA Chips and Mircoarrays: II", Science Magazine, pp. 1-18, (2004), <www.sciencemag.org>.

Meldrum, Deirdre, "Automation for Genomics, Part One: Preparation for Sequencing", Genome Research, Cold Spring Harbor Labratory Press ISSN 10898-9051/00, pp. 1081-1092, (2000), <www.genome.org>.

"Agilent Microarray Services", Service SX, pp. 1-2, <www.servicesxs.com>.

"Agilent SurePrint Technology", Agilent Technologies, pp. 1-2, <www.chem.agilent.com>.

Seiko Epson Corportion et al., "Pico Liter Dispenser with 128 Independent Nozzles for High Throughput Biochip Fabrication", pp. 276-279, (2004).

* cited by examiner

MICROTRAY FOR HANDLING BIOSUBSTANCES

BACKGROUND

With the hope of finding new drugs and unlocking the secrets of the genetic code, companies have aggressively pursued technology for handling biological materials. One technology area of particular interest includes liquid handling and/or high throughput screening, which attempts to process hundreds or thousands of samples of substances in parallel to rapidly determine a property of those substances. Typically, a first set of substances are provided on a chip or substrate while a second set of substances are applied to the first set of substances to identify any useful interactions. Systems for performing high throughput screening and/or liquid handling include various functions such as filling reservoirs, aspirating liquids from those reservoirs, and dispensing fluids into testing reservoirs. Liquids are ultimately deposited onto substrates, such as a slide, or into holding reservoirs such as a microplate with an array of wells.

Unfortunately, despite heavy pursuit of simplification in this technology area, these high throughput screening systems or liquid handling systems, are still fairly cumbersome. Fluids are placed into reservoirs for storage using one type of device, such as a micropipette system, and then using a separate type of device such as a quill pin system, fluids are drawn from the reservoirs and then dispensed into other wells, onto chips as arrays, or onto slides. With each additional step of handling, the chances increase of making errors in maintaining the intended state of the biological material. Moreover, the systems for performing these tasks can be rather bulky since separate subsystems are used for each desired function, for example, these systems may include a micropipette for filling, a microplate for holding a substance or receiving test reagents, a dispensing mechanism for dispensing fluids from the microplate onto a slide, etc.

In addition, conventional liquid handling systems use relatively larger volumes of biological materials due to the larger size and/or lack of precision associated with conventional liquid dispensing devices. Conventional liquid handling systems also typically require frequent steps of washing and/or rinsing components of the system, which wastes time and resources.

For these reasons, among others, systems for liquid handling of biological materials have yet to achieve their full potential.

DETAILED DESCRIPTION

Figure 1:
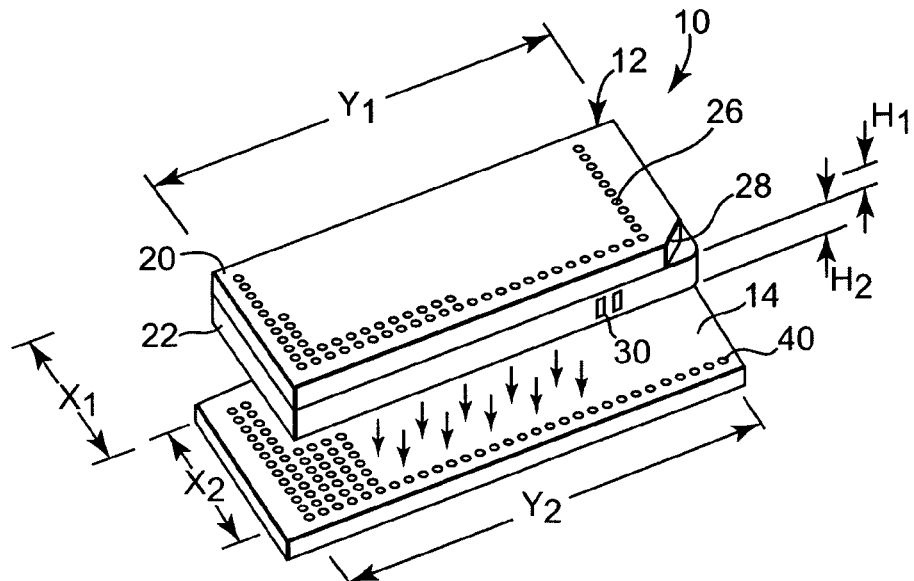
FIG. 1 is an isometric view of a microtray, according to an embodiment of the present invention.

In the following detailed description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Embodiments of the present invention are directed to a microtray system configured for handling liquids such as biological substances. Biological substances (herein "biosubstances") includes biological flowable materials which includes, but is not limited to, human fluids, cells, and/or cell components, animal fluids, cells, and/or cell components, plant fluids cells, and/or cell components, other cellular components, as well as non-cellular biological materials including, but not limited to, proteins, antibodies, antigens, RNA, DNA, oligonucleotides, nucleotides, nucleosides, sugars, lipids, cytokines, etc. In one embodiment, biosubstances also include fluid mediums which act as a carrier to enable biological materials to flow for handling with a microtray. In another embodiment, biosubstances also include materials capable of affecting biological materials, such as chemicals, pharmaceutical agents, reagents, etc.

In one embodiment, biosubstances comprise oligonucleotides such as those provided in microarrays, as well as those biological materials typically handled in microvolume liquid handling systems.

In another embodiment, a microtray acts as a liquid handler for handling general chemicals that do not necessarily affect or relate to biologic materials, properties, causes or effects. Accordingly, in one embodiment, the term "chemical" can be substituted generally for the term "biosubstance" in relation to the function being served by a microtray, such as filling, mixing, heating, routing, ejecting, etc. of chemicals instead of biosubstances.

In one embodiment, a microtray is an active device which holds biosubstances in an array of wells and then also dispenses the biosubstances onto a target media, such as a glass slide for building a microarray or such as wells of a microplate. The microtray comprises a fluid holding structure and a fluid ejection structure in fluid communication with the fluid holding structure. The fluid holding structure comprises an array of wells, which supply the fluid ejection structure with biosubstances to be dispensed. The fluid ejection structure comprises an array of fluid ejection devices. In one embodiment, these fluid ejection devices act as ejection ports and are configured to generate a force within the fluid ejection structure on a microvolume of the biosubstances to cause the biosubstances to be ejected from the ejection ports as a drop (s) onto the target media. In another embodiment, these fluid ejection devices comprise at least one thermal drop-on-demand ejection device or other drop-generating mechanisms (e.g., piezoelectric or flex-tensional), which selectively dispense microvolumes of biosubstances onto the target media without the ejection device contacting the target media (i.e., non-contact dispensing).

In one embodiment, a microtray is an active device that has the look, feel, and sizing of a conventional passive microplate, thereby enabling its use for holding biosubstances in conventional liquid handling systems. However, this microtray is also capable of active functions such as dispensing fluids supplied from the fluid holding structure of the microtray, thereby enabling use of the microtray in entirely new schemes of liquid handling and microarray deposition. Accordingly, in another embodiment, a microtray is not limited to the sizes and shapes of conventional microplates, since this microtray is capable of operating significantly differently than conventional microplates.

Moreover, a microtray of embodiments of the present invention is not strictly limited to handling microliter volumes of fluids as the term "micro" refers more generally to the general field of liquid handling systems (e.g. high throughput screening, other array handling mechanisms), microtiters, microarrays, etc. which involve handling a range of volumes of fluids and in which the devices, such as microplates, that are used to handle the volumes have some dimensions (e.g. any one or more of well volumes, well density, well pitch, certain lengths or widths, footprint, array population, spot pitch, spot size, spot volumes, etc.) that are typically on the micron scale of measurement. Accordingly, one or more microtrays are in embodiments of the invention configured to handle (e.g. hold and/or dispense) biosubstances in volumes such as milliliter volumes, microliter volumes, nanoliter volumes, picoliter volumes, and/or femptoliter volumes.

The term "microvolume" of a biosubstance in this document refers generally to small scale volumes of fluids and includes volumes in the ranges of milliliter volumes, microliter volumes, nanoliter volumes, picoliter volumes, and femptoliter volumes, with these specific volume ranges being referenced by their respective prefix-liter designation.

In one embodiment, a microvolume drop of a biosubstance (e.g. milliliter, microliter, nanoliter, picoliter, femptoliter, etc.) from a single well of a fluid holding structure is dispensed using a single ejection device (including a single or multiple nozzles) of the fluid ejection structure. Each ejection device can eject drops that are substantially the same size, or each ejection device can eject a different size drop. In one embodiment, each ejection device has several nozzles of different sizes to thereby eject different volumes of biosubstances (e.g., milliliter, microliter, nanoliter, picoliter, fempto, etc) from the respective nozzles. Accordingly, differently-sized volumes of the same biosubstance are dispensed adjacent each other via adjacently-placed nozzles of a single ejection device. In another embodiment, the multiple nozzles associated with the single ejection device are substantially the same size, thereby producing substantially the same size drop from each nozzle.

In another embodiment, a drop of a biosubstance is dispensed in a selected volume (e.g., milliliter, microliter, nanoliter, picoliter, femptoliter, etc.) by using multiple nozzles of an ejection device of the fluid ejection structure in a coordinated manner to produce the selected volume drop for depositing on a target surface (e.g., slide, well, etc.).

In another embodiment, a microtray comprises a fluid processing structure sandwiched between a top fluid holding structure and a bottom fluid ejection structure. The fluid processing structure enables performing various operations on biosubstances prior to ejection onto a target media. These operations include mixing, reacting, filtering, etc. one or more biosubstances to yield altered biosubstances, combined biosubstances, and/or new biosubstances. In one embodiment, two or more different biosubstances are processed via the fluid processor structure to create a new biosubstance. Accordingly, placing these functions within the microtray virtually eliminates conventional arduous steps of moving biosubstances between different plates or slides via micropipettes, quill pin systems, aspirators and other devices. Instead, these operations are performed on biosubstances within a single microtray that also holds biosubstances and dispenses biosubstances out of the microtray on demand. In other embodiments, this microtray including a fluid processor structure handles chemicals (e.g. holding and/or dispensing) that need not be biosubstances. Accordingly, this microtray mimics a liquid handling system rather than merely being a passive fluid holder. This microtray including a fluid processor structure may or may not be substantially the same size and shape as conventional microplates.

In one embodiment, the microtray includes circuitry to operate the fluid ejection structure and/or fluid processor structure and includes input/output (I/O) contact pads for electrical communication with a control station, which also includes electrical contact I/O pads for interfacing with the active microtrays. Via these respective I/O pads of the microtray and control station, microtray receives power and instructions for operation. In one embodiment, an aspect of the control station releasably secures the microtray in a fixed position to enable movement of a target media relative to the microtray, thereby enabling higher density applications of drops or spots of biosubstances on a target media. In another embodiment, an aspect of the control station enables the microtray to be moved relative to a stationary or moving target media during dispensing of the biosubstances.

Finally, in another embodiment, a fluid ejection structure of microtray embodies thermal inkjet-type technology to enable dispensing volumes of biosubstances as low as 5 picoliters, or even lower volumes in the femptoliter volume range. Accordingly, the size of wells that supply fluid to each fluid ejection device can be much smaller, which thereby enables much smaller microtrays carrying densities of 6144 wells per microtray. When used as a microplate, this density creates a new smaller form factor for ANSI-standard-sized microplates of 6144 wells per microplate. Accordingly, this microtray enables carrying about 4 times more unique biosubstances within wells of a single microtray than possible with a conventional ANSI/SBS standard microplate. Moreover, in one embodiment, the microtray can dispense fluid from each well of the fluid holding structure via a uniquely corresponding group of fluid ejection devices of the fluid ejection structure onto the target media. This direct one-to-one correspondence between each well and a group of ejection devices, in turn, increases the precision and accuracy of biosubstance printing, enabling an increased density of unique spots of biosubstances being applied per surface area of the target media.

With these features, among others, embodiments of the present invention greatly simplify handling of biosubstances, and increase the precision and accuracy of depositing biosubstances as microarrays and onto other targets, such as glass slides and/or wells of microplates. Within a single microtray, biosubstances can be stored, processed with property-altering operations or combined, and then dispensed in extremely minute volumes. These capabilities will overcome many problems associated with conventional handling biosubstances, such as in situ building of oligonucleotides.

FIG. 1 illustrates one embodiment of a microtray system 10 according to the present invention. Microtray system 10 comprises one embodiment of a fluid handling system which includes a microtray 12 and a target media 14, such as microplate. Microtray 12 comprises fluid holding structure 20 including an array of wells 26 or reservoirs, and fluid ejection structure 22, which acts as a dispenser for dispensing fluids as an array of spots on target media 14. Microtray 12 also comprises electrically conductive input/output contact elements 30 to enable electrical communication with circuitry within fluid ejection structure 22. In one embodiment, microtray 12 has the look and feel of a microplate, having substantially the same footprint (X1 by Y1), height (H1 and H2), well position (X2, Y2), well count (# of wells), chamfer 28 and flange configuration etc, of an ANSI/SBS standard microplate. For example, in one embodiment, microtray 12 has a length Y1 of about 125 millimeters, a width X1 of about 85 millimeters, a combined height (H1+H2) of about 14 millimeters of fluid holding structure 20 (H1) and of fluid ejection structure 22. However, in addition to holding fluids in wells 26 of fluid holding structure 20, fluid ejection structure 22 of microtray 12 is configured to dispense fluids obtained from wells 26 onto target media 14 via a drop-generating mechanism (e.g., thermal, piezoelectric, or flex-tensional) within fluid ejection structure to move drops of fluids out of fluid ejection structure 22.

In one embodiment, microtray 12 comprises a single structure in which both fluid holding structure 20 (e.g., a first layer) and fluid ejection structure 22 (e.g., a second layer) formed together as a monolithic structure. In another embodiment, microtray 12 comprises fluid holding structure 20 and fluid ejection structure 22 defining separate elements that are joined together to define a single structure.

In one embodiment, target media 14 comprises a substrate or work surfaces, such as a slide configured to receive biological substances deposited onto its upper surface. In one embodiment, target media 14 comprises a conventional microplate with an array of wells 40 for receiving drops dispensed by microtray 12. In another embodiment, target media 14 comprises a microplate with a footprint (e.g., length, width), height, and well positions (e.g. densities of 96, 384, 1536 wells per microplate) in accordance with microplate standards under American National Standards Institute/Society for Biomolecular Screening (SBS), including ANSI/SBS 1-2004, 2-2004, 3-2004 and 4-2004.

In another embodiment, target media 14 comprises a microplate that meets the ANSI/SBS standards for footprint and height of conventional microplates, but further comprises well positions in new form factors having greater densities than those specified in the standards, such as a density of 6144 wells per microplate, in accordance with embodiments of the present invention.

Figure 5:
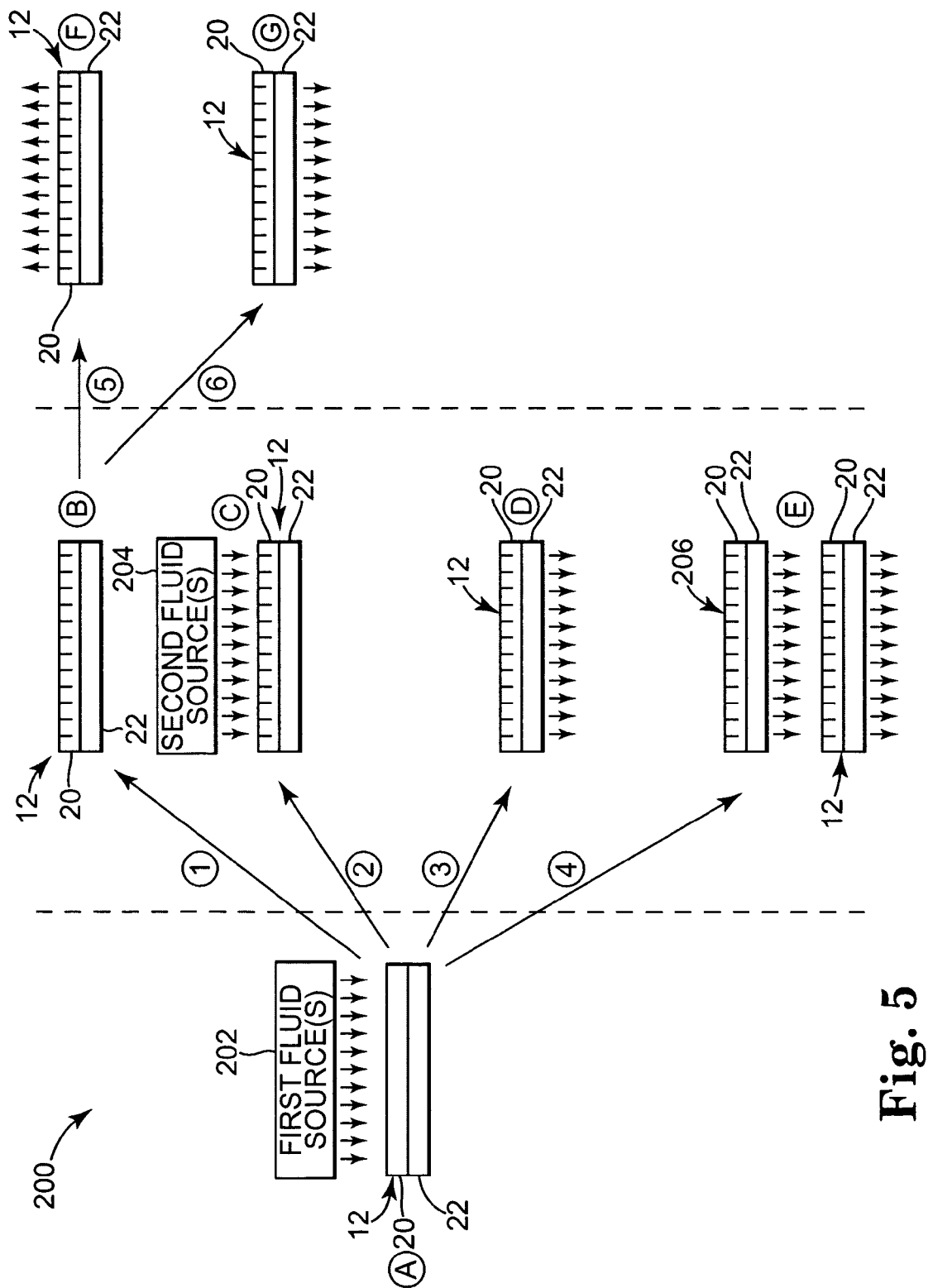
FIG. 5 is a schematic illustration of a method of handling substances with a microtray, according to an embodiment of the present invention.

Finally, in another embodiment, target media 14 comprises a second microtray having substantially the same features and attributes as microtray 12 except placed below fluid ejection structure 22 of microtray 12 to receive dispensed drops of biosubstances into an array of wells of a fluid holding structure of the second microtray. This embodiment is described further in association with the embodiments of FIG. 5.

In one embodiment, each well 26 holds a unique biosubstance different than biosubstances in the other wells 26 of fluid holding structure 20. In another embodiment, each well 26 holds substantially the same biosubstance in each well 26 of fluid holding structure 20. In another embodiment, the same biosubstance is held in more than one well 26 of fluid holding structure 20, but not in all wells 26 of fluid holding structure 20.

Figure 2:
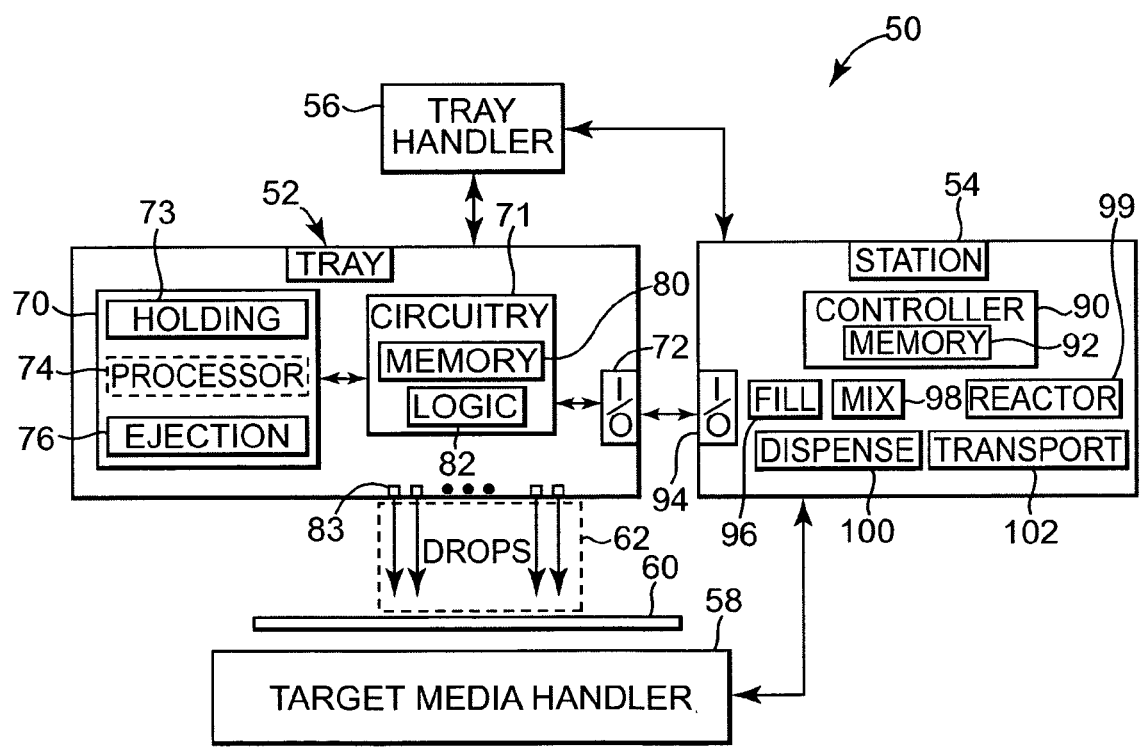
FIG. 2 is a block diagram of a microtray system, according to an embodiment of the present invention.

FIG. 2 illustrates one embodiment of microtray system 50 for handling biosubstances and comprises microtray 52, station 54, tray handler 56, and target media handler 58 supporting target media 60.

Microtray 52 has substantially the same features and attributes as microplate 12. Microplate 52 comprises fluid handling components 70, circuitry 71, and input/output interface 72. Fluid handling components 70 include, but are not limited to, fluid holding structure 73, fluid processor 74, and fluid ejection structure 76. Circuitry 71 comprises electrical components suitable for operating an electrically activatable liquid ejection device and includes, but is not limited to, memory 80 and logic 82. Station 54 comprises controller 90 with memory 92, input/output interface 94, filling module 96, mixing module 98, dispensing module 100, and transport module 102.

Microtray 52 ejects drops of fluid, including one or more biological substances such as liquids, fluids, and other flowable materials, through a plurality of orifices or nozzles 83. In one embodiment, drops produced from fluid ejection structure 76 are on the order of about 5 picoliters in volume, which is understood to be about 4-5 times smaller than volumes produced by conventional piezoelectric drop-on-demand ejection technology.

In one embodiment, the drops are directed toward a medium, such as target media 60, so as to print onto target media 60. Typically, nozzles 83 are arranged in one or more columns or arrays such that properly sequenced ejection of fluid (e.g. biosubstances) from nozzles 83 causes, in one embodiment, an array of spots to be printed upon target media 60 as microtray 52 and target media 60 are moved relative to each other.

Fluid holding structure 73, as one embodiment of a fluid supply, supplies fluid to fluid ejection structure 76 and includes one or more reservoirs for storing fluids. As such, fluid flows directly from fluid holding structure 73 to fluid ejection structure 76. In one embodiment, a fluid processor 74 (e.g., a third layer) is interposed between fluid holding structure 73 (e.g., a first layer) and fluid ejection structure 76 (e.g., a second layer). In another embodiment, fluid processor 74 is omitted and fluid holding structure is in direct fluid communication with fluid ejection structure 76. One embodiment of fluid processor 74 is later described in more detail in association with the embodiment of FIG. 10.

Tray handler 56 positions microtray 52 relative to target media handler 58, and target media handler 58 positions target media 60 relative to microtray 52. As such, a print zone 62 within which microtray 52 deposits fluids, such as biosubstances, is defined adjacent to nozzles 83 in an area between microtray 52 and target media 60. Target media 60 is held stationary or advanced through print zone 62 during printing by target media handler 58.

In one embodiment, microtray 52 includes a scanning type fluid ejection structure 76, and tray handler 56 moves microtray 52 relative to target media handler 58 and target media 60 during printing of a pattern of biosubstances on target media 60. In another embodiment, microtray 52 includes a non-scanning type fluid ejection structure 76, and tray handler 56 fixes microtray 52 at a prescribed position relative to target media handler 58 during printing of a pattern of biosubstances on target media 60 as target media handler 58 advances target media 60 past the prescribed position.

Electronic controller 90 of station 54 communicates with microtray 52, tray handler 56, and target media handler 58. In one embodiment, electronic controller 90 receives instructions and data from a host system, such as a computer, and includes memory 92 for temporarily storing those instructions and data. Typically, data is sent to microtray system 50 along an electronic, infrared, optical or other information transfer path. In another embodiment, station 54 including controller 90 is self-supporting, i.e., including its own instructions and data supplied through a user interface and/or stored in memory 92. In either embodiment of controller 90, these instructions and data represent, for example, an instruction set specifying a request for depositing an array of biosubstances from microtray 52 onto target media 60. As such, these instructions and data form a bioprinting job for microtray system 50 and includes one or more bioprinting commands and/or command parameters that dictate operation of the components of microtray system 50.

As shown in the embodiment of FIG. 2, station 54 comprises various modules 92-102 for supporting operation of microtray 52 to handle biosubstances. In one embodiment, filling module 96 of station 54 enables filling wells of fluid holding structure 73 of microtray 52 with biosubstances from a source external to microtray 52. In one embodiment, mixing module 98 of station 54 supports mixing of different biosubstances (e.g. different in quantity, type, concentration, etc.) in fluid processor 74, prior to dispensing via fluid ejection structure 76 of microtray 52. In one embodiment, reactor module 99 of station 54 supports reacting of different biosubstances in fluid processor 74 prior to dispensing via fluid ejection structure 76 of microtray 52. In one embodiment, dispensing module 100 of station 54 enables control over activation and deactivation of one or more nozzles 83 of fluid ejection structure 76 of microtray 52. In one embodiment, transport module 102 of station 54 enables positioning of target media 60, via target media handler 58, relative to microtray 52, and/or positioning of microtray 52, via tray handler 56, relative to target media 60.

In one embodiment of station 54, electronic controller 90 provides control of microtray 52 including timing control for ejection of fluid drops from nozzles 83. As such, electronic controller 90 defines a pattern of ejected drops of biosubstances which form an array of spots on target media 60. Timing control and, therefore, the pattern of ejected drops of biosubstances, is determined by the job commands and/or command parameters held in memory 92 of station 54 or in memory 80 of circuitry 71 of microtray 52. In one embodiment, logic and drive circuitry forming a portion of electronic controller 90 is located in station 54 externally of fluid ejection structure 76 of microtray 52. In another embodiment, logic and drive circuitry forming a portion of electronic controller 90 is formed as part of circuitry 71 of fluid ejection structure 76 of microtray 52.

Microtray 52 is formed from a silicon, glass, or stable polymer, using semiconductor and thin-film microfabrication techniques, known to those skilled in the art, enabling the formation of various structures of microtray 52 such as wells, channels, operational components of fluid processor 74, and ejection devices. Materials and fabrication techniques for forming fluid ejection structure 76 are later described in more detail in association with the embodiment of FIG. 4A.

Finally, microtrays 12, 52 of the embodiments of FIGS. 1-2 can be configured to meet different form factors. In one embodiment, the fluid holding structure and the fluid ejection structure of a microtray are formed as an ANSI/SBS standard microplate having a length, a width, and a height configured to enable one of three arrangements. In a first arrangement, microtray 12, 52 is formed substantially similar to a microplate with a first array of 96 wells in the fluid holding structure having a pitch between adjacent wells of about 9 millimeters and a density of about 1 well per square centimeter over a surface of the microplate. In a second arrangement, microtray 12, 52 is formed substantially similar to a microplate with a second array of 384 wells in the fluid holding structure having a pitch between adjacent wells of about 4.5 millimeters and a density of about 3.5 wells per square centimeter over a surface of the microplate. In a third arrangement, microtray 12, 52 is formed substantially similar to a microplate with a third array of 1536 wells in the fluid holding structure having a pitch between adjacent wells of about 2.25 millimeters and a density of about 14 wells per square centimeter over a surface of the microplate.

In another embodiment, a microtray comprises a fluid holding structure and the fluid ejection structure formed together and having a length, width, and height meeting the ANSI/SBS microplate standard yet configured to enable a fourth array of 6144 wells in the fluid holding structure with a pitch between adjacent wells of about 1.125 millimeters and a density of about 56 wells per square centimeter over a surface of the microplate.

Accordingly, microtrays 12, 52 enable meeting known form factors for microplates and enable exceeding those form factors to create new form factors for microplates, as well as creating whole new functions (e.g., processing, dispensing, etc.) not previously associated with conventional microplates.

Figure 3:
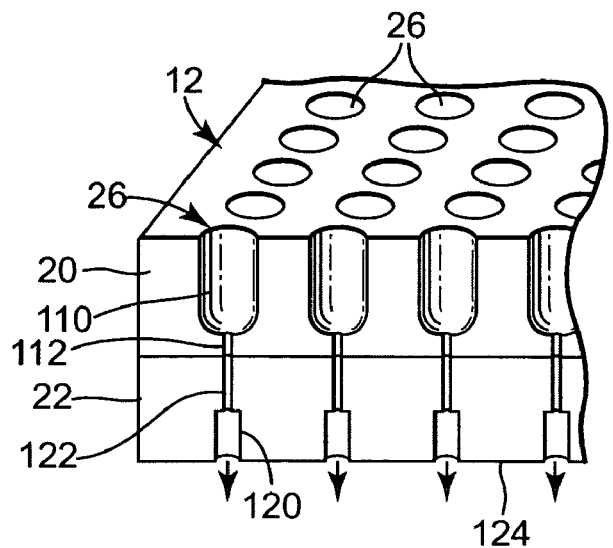
FIG. 3 is partial sectional view of a microtray, according to an embodiment of the present invention.

FIG. 3 is a partial sectional view of one embodiment of microtray 12, 52. As shown in FIG. 3, microtray 12 comprises fluid holding structure 20 and fluid ejection structure 22 with fluid holding structure 20 including wells 26 having a body 110, necked outlet 112 and fluid ejection structure 22 having drop-ejection devices 120 with inlets 122. Each well 26 has a direct, unique correspondence to one of the respective drop-ejection devices 120. As such, drop-ejection devices 120 can eject as many unique biological substances as can be separately provided in wells 26. Drop-ejection devices 120 are later described in more detail in association with the embodiment of FIG. 4.

Figure 6:
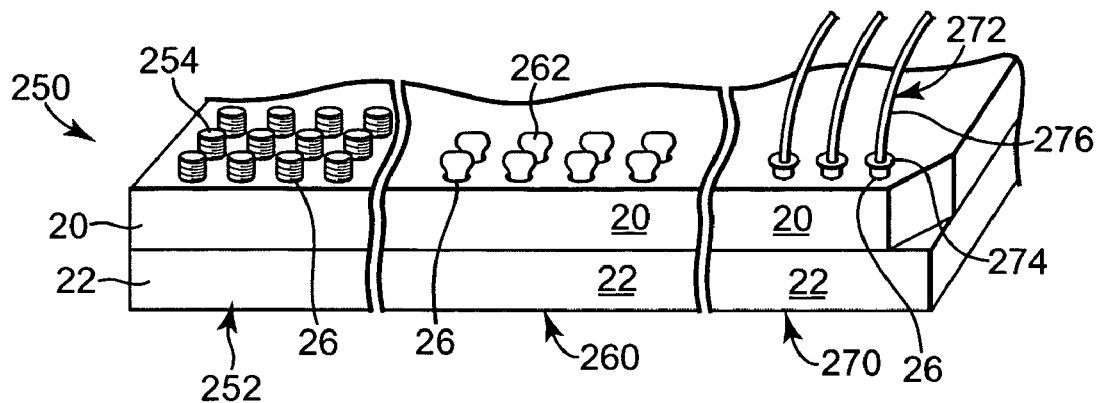
FIG. 6 is partial sectional view of a microtray, according to an embodiment of the present invention.

In one embodiment of fluid holding structure 20, body 110 of wells 26 have a diameter that is sufficiently small and a length (i.e., height as seen in FIG. 3) that is sufficiently large to create a capillary fluid effect on biosubstances within wells 26. This effect, in turn, exerts a back pressure on biosubstances extending from each well into a respective drop-ejection device 120, such as a thermal fluid ejection device. This back pressure prevents drooling (e.g. unwanted dripping) of biosubstances from drop-ejection devices 120. Minimizing drooling conserves the biosubstances and insures that biosubstances are not errantly deposited on a target media 14,60 (FIGS. 1-2). Other embodiments of back pressure mechanisms to prevent drooling are later described in association with the embodiments of FIGS. 6-8.

Figure 4A:
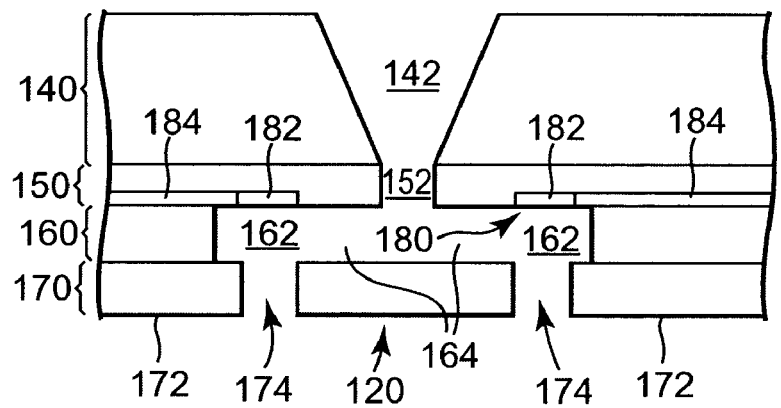
FIG. 4A is a partial sectional view of a microtray, according to an embodiment of the present invention.
Figure 4B:
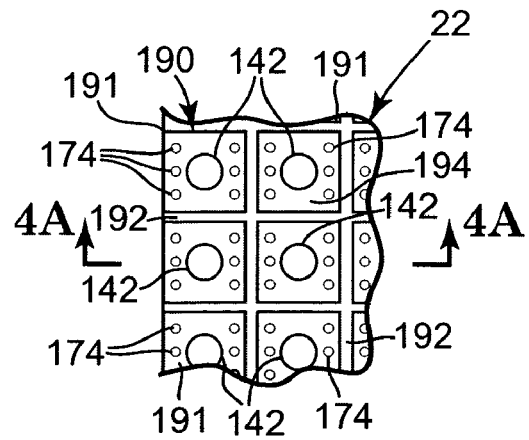
FIG. 4B is partial top view of a fluid ejection structure of a microtray, according to an embodiment of the present invention.

FIG. 4A illustrates one embodiment of a portion of fluid ejection structure 22 of microtray(s) 12, 52. In one embodiment, fluid ejection structure 22 includes an array of drop ejecting elements 120 (e.g., ejection ports). Drop-ejecting element(s) 120 shown in FIGS. 4A-4B is just one architecture (e.g. geometrical arrangement of components) of a liquid ejection device shown for illustrative purposes, as other thermal fluid ejection devices are capable of dispensing microvolumes of fluid in a non-contact manner. In one embodiment, one or more drop-ejecting element 120 dispenses a volume per drop in a range of volumes from milliliters to picoliters, such as 5 picoliters, as well as volumes in the range of femptoliters.

Drop-ejecting elements 120 are formed on a substrate 140 which has a fluid (or biosubstance) feed hole 142 formed therein, such as fluid inlet 122 (FIG. 3) which is not limited to the size and shape shown in FIG. 3. As such, fluid feed hole 142 provides a supply of fluid (or biosubstance) to more than one drop-ejecting elements 120. In one embodiment, fluid feed hole 142 generally corresponds to a fluid inlet such as inlet 122 (which is in fluid communication with a well 26) of the embodiment of drop-ejecting element 120 of FIG. 3.

In one embodiment, each drop-ejecting element 120 includes a thin-film structure 150, a barrier layer 160, an orifice layer 170, and a drop generator 180. Thin-film structure 150 has a fluid (or biosubstance) feed opening 152 formed therein which communicates with fluid feed hole 142 of substrate 140 and barrier layer 160 has a fluid ejection chamber 162 and one or more fluid channels 164 formed therein such that fluid ejection chamber 162 communicates with fluid feed opening 152 via fluid channels 164.

Orifice layer 170 has a front face 172 and an orifice or nozzle opening 174 formed in front face 172. In one embodiment, orifice layer 170 corresponds to a lower surface of microtray 12, 52 (FIGS. 1-2). As shown in FIG. 4, orifice layer 170 is extended over barrier layer 160 such that nozzle opening 174 communicates with fluid ejection chamber 162. In one embodiment, drop generator 180 includes a resistor 182. Resistor 182 is positioned within fluid ejection chamber 162 and is electrically coupled by leads 184 to drive signal(s) and ground.

While barrier layer 160 and orifice layer 170 are illustrated as separate layers, in other embodiments, barrier layer 160 and orifice layer 170 may be formed as a single layer of material with fluid ejection chamber 162, fluid channels 164, and/or nozzle opening 174 formed in the single layer. In addition, in one embodiment, portions of fluid ejection chamber 162, fluid channels 164, and/or nozzle opening 174 may be shared between or formed in both barrier layer 160 and orifice layer 170.

In one embodiment, during operation, fluid (e.g. a biosubstance) flows from fluid feed hole 142 to fluid ejection chamber 162 via fluid feed opening 152 and one or more fluid channels 164. Each nozzle opening 174 is operatively associated with its own resistor 182 such that droplets of fluid are ejected from each fluid ejection chamber 162 through the respective nozzle opening 174 (e.g., substantially normal to the plane of resistor 182) and toward a target medium (e.g., target media 60 in FIG. 2) upon energization of resistor 182.

In one embodiment, each drop-ejecting element 120 comprises a single nozzle opening 174 with its associated resistor 182, chamber 162, and channel 164. As such, FIG. 4A would be understood to schematically depict two drop-ejecting elements 120. In another embodiment, each drop-ejecting element 120 comprises more than one nozzle opening 174 with a shared channel 164. As such, FIG. 4A would be understood to schematically depict one drop-ejecting element 120 having two nozzle openings 174, each opening having its own resistor 182.

Resistor 182 is energized by sending a current thru it. Energy applied to the resistor is controlled by applying a fixed voltage to the resistor for a duration of time. In one embodiment, energy applied to the resistor is represented by the following equation:

$$\text{Energy} = ((V*V)*t)/R$$

where V is the voltage applied, R is the resistance of the resistor, and t is the duration of the pulse. Typically, the pulse is a square pulse.

In one embodiment, resistor 182 is connected to a switch which in turn is connected in series to a power supply. Resistor 182 comprises an arrangement of one or more resistors configured in suitable configurations for applying energy to biosubstances within fluid ejection chamber 162.

In one embodiment, liquid ejection structure 22 is a fully integrated thermal fluid ejection device, such as a thermal inkjet printhead. As such, substrate 140 is formed, for example, of silicon, glass, or a stable polymer, and thin-film structure 150 includes one or more passivation or insulation layers formed, for example, of silicon dioxide, silicon carbide, silicon nitride, tantalum, poly-silicon glass, or other material. Thin-film structure 150 also includes a conductive layer which defines resistor 182 and leads 184. The conductive layer is formed, for example, by aluminum, gold, tantalum, tantalum-aluminum, or other metal or metal alloy. In addition, barrier layer 160 is formed, for example, of a photoimageable epoxy resin and orifice layer 170 is formed of one or more layers of material including, for example, a metallic material, such as nickel, copper, iron/nickel alloys, palladium, gold, or rhodium. Other materials, however, may be used for barrier layer 160 and/or orifice layer 170.

Accordingly, with these features, drop ejection elements 120 enable drop-on-demand, non-contact dispensing of biosubstances as microvolumes as little as 5 picoliters per drop dispensed. With this architecture, in one embodiment, microtrays 12, 52 (FIGS. 1-2) comprises a density of at least 6144 drop-ejection elements 120 per microtray 12, which substantially exceeds the ANSI/SBS microplate standards of maximum well density of 1534. Moreover, in some embodiments of microtrays 12, 52 have a well density of 6144 wells per microtray with more than one drop-ejection element 120 corresponding to each well, which in turn enables very large arrays of separate volumes of unique biosubstances to be deposited concurrently from microtray 12, 52. However, even though the drop-ejection elements 120 are sufficiently small to enable these high densities, microtray 12, 52 can have lower densities of wells and nozzles, and still enjoy precision and accuracy in dispensing microvolumes of biosubstances as low as 5 picoliters per spot, or even lower.

FIG. 4B is a partial top view schematically depicting one embodiment of a fluid ejection structure 22 (FIG. 1) of a microtray. As shown in FIG. 4B, fluid ejection structure 22 comprises an array 190 of fluid ejection units 191. Each unit 191 comprises fluid feed hole 142 (FIG. 4B) and a plurality of drop ejection elements (represented by nozzle openings 174), such as drop-ejection elements 120 (FIG. 4A). As shown in FIG. 4B, nozzle openings 174 are represented by lighter lines than fluid feed hole(s) 142 to indicate the presence of nozzle openings 174 at a different, lower elevation than fluid feed hole 142. This elevational difference corresponds to the arrangement in the embodiment of FIG. 4A. Barriers 192 maintain separation between adjacent fluid ejection units 191 and also define a boundary for an interior 194 of each unit 191. With this arrangement, a single fluid feed hole 142, which corresponds to a single well 26 (FIG. 1 or 3) supplies fluid to multiple drop-ejection elements 120, i.e., nozzle openings 174 with corresponding drop generators 180 (FIG.

4A). While six nozzle openings 174 are associated with a single fluid feed hole 142, other arrangements are contemplated with either a greater number of nozzles per fluid feed hole 142 (e.g., 10), or a lower number (e.g., 4) depending upon the number of fluid feed holes 142 (corresponding to wells 26) on a single microtray 12. In one embodiment, the number of nozzles 174 per fluid feed hole 142 will increase when there are fewer number of wells per microtray, and conversely the number of nozzle openings 174 per fluid feed hole 142 will decrease with a relatively greater number of wells per microtray. Accordingly, in this embodiment, a single well 26 of a fluid holding structure 20 of a microtray, as represented by fluid feed hole 142, supplies fluid to multiple drop-ejection elements 120 (FIG. 4A).

In one embodiment, using multiple nozzles to dispense the same biosubstance from a single well, via fluid feed hole 142, as side-by-side spots on a target media (e.g., target media 60) enables the target media to carry duplicate spots of the same biosubstance. This spot duplication, enabled by multiple nozzles per well, permits using experimental replicates, thereby increasing the accuracy of tests using that biosubstance. This multiple nozzle per well arrangement also provides an effective mechanism to achieve redundancy in spotting onto a target media, so that if a single spot of a biosubstance produces an error or is defective in some manner, another identical spot of the same biosubstance can take the place of the defective spot. In one embodiment, there are as many duplicate drops of biosubstances dispensed as spots onto a target media as there are nozzles per fluid feed hole 42 (associated with a single well 26). In another embodiment, some of these nozzles associated with a single fluid feed hole 42 produce differently-sized drops, so that some of the duplicate spots of the same biosubstance have different volumes, thereby providing another level experimental robustness if a particular volume spot fails to achieve a successful result.

FIG. 5 schematically illustrates one embodiment of a method 200 of handling biosubstances with microtray 12 of the embodiment of FIGS. 1-4B. In one embodiment, microtray 12 also corresponds to microtray 52 of the embodiment of FIG. 2.

As shown in FIG. 5, in a first state A of operation, first fluid source(s) 202 fills fluid holding structure 20 of microtray 12 with one or more biosubstances. As further shown in FIG. 5, microtray 12 is then used in one or more of states of operation B, C, D, E. Directional arrows 1, 2, 3, and 4 represent handling of microtray 12 in association with a station (such as station 54 of the embodiment of FIG. 2) to enable operation in one of states B, C, D, E.

Second state B of operation of microtray 12 comprises storing biosubstances within the wells of fluid holding structure 20 of microtray 12 until some suitable time period when another operation is to be performed using those biological substances. In one embodiment, microtray 12 comprises a fluid holding structure 20 including at least 6144 wells (e.g., wells 26 FIGS. 1 and 3), with each well configured to hold at least one biosubstance and/or chemical. In this embodiment, this microtray 12 functions as a passive microplate, merely holding biosubstances (or chemicals) within wells 26. At a later time, biosubstances within fluid holding structure 20 are withdrawn via other mechanisms, or ejected through fluid ejection structure 22. Biosubstances or chemicals can be filled into the at least 6144 wells of microtray 12 via another microtray 12 or other dispensing mechanism.

In another embodiment, microtray 12 comprises the fluid holding structure 20 with at least 6144 wells wherein after the biosubstances are held in microtray 12 for a period of time, an ejection mechanism different than fluid ejection structure 22 receives the biosubstances from wells 26 of fluid holding structure 20 and dispenses the biosubstances. This different ejection mechanism may or may not be directly connected to microtray 12. Accordingly, once fluid holding structure 20 of microtray 12 holds biosubstances within its well, microtray 12 is not strictly limited in its use to ejecting a biosubstance via fluid ejection structure 22.

Third state C of operation of microtray 12 comprises adding a second volume of biosubstances from a second fluid source(s) 204 into one or more wells of fluid holding structure 20 of microtray 12. Accordingly, the first volume of biosubstances from the first fluid source(s) 202 (added in operational state A) are necessarily mixed with the second volume of biosubstances within individual wells of fluid holding structure 20 of microtray 12.

Fourth state D of operation of microtray 12 comprises dispensing the biosubstances from wells of fluid holding structure 20 onto a target media via fluid ejection structure 22.

Fifth state E of operation of microtray 12 comprises positioning a second microtray 206 relative to microtray 12 to enable additional filling of fluid holding structure 20 of microtray 12 with biosubstances from microtray 206. Alternatively, in another embodiment, the position of microtray 206 and microtray 12 are reversed, so that microtray 12 fills fluid holding structure 20 of microtray 206, from which volumes of mixed biosubstances are then dispensed via fluid ejection structure 22. Accordingly, multiple microtrays can be positioned in a vertically stacked, spaced arrangement for filling and/or dispensing relative to one another. In one embodiment, more than two microtrays can be stacked vertically for filling and/or dispensing operations relative to one another.

Sixth state F of operation of microtray 12 comprises using microtray 12 that has been storing biosubstances (e.g., second state B of operation) and aspirating the biosubstances out of the fluid holding structure.

Seventh state G of operation of microtray 12 comprises using microtray 12 that has been storing biosubstances (e.g., second state B of operation) for an extended period of time and dispensing the biosubstances in a manner, substantially similar to fourth state D of operation of microtray 12.

FIG. 5 merely illustrates various operational states of single microtrays 12 and multiple microtrays 12, 206 as examples of using microtrays. Accordingly, embodiments of the present invention of microtrays are not limited to these operational states A-G of using microtray 12.

FIG. 6 illustrates embodiments of back pressure devices mounted on a top surface of a fluid holding structure of a microtray to insure proper back pressure is applied to drop-ejection devices within fluid ejection structure. As shown in FIG. 6, back pressure system 250 comprises any one or more of back pressure devices 254, 262, and/or 272. In one embodiment, microtray 252 comprises back pressure devices 254 which are formed as bellow-shaped reservoirs mountable separately into and/or over each respective well to exert back pressure on a corresponding fluid ejection device.

In one embodiment, microtray 260 comprises back pressure devices 262 which are formed as bladder-type reservoirs mountable separately into and/or over each respective well to exert back pressure on a corresponding fluid ejection device. These bladder-type reservoirs also carry a volume of biological substance for filling a corresponding well over which the bladder reservoirs are mounted. Further details regarding these bladder-shaped back pressure devices 262 are described and illustrated in association with the embodiment of FIGS. 7A, 7B.

In one embodiment, microtray 270 comprises hose assemblies 272, which include connector 274 and hose 276. Each connector 274 fits into or over each well of fluid holding structure 20 to permit separate filling of each well from a uniquely corresponding hose assembly 272. In addition to supplying biosubstances through hose 276 to wells 26 from external sources, these fluid-filled hoses 276 also exert a back pressure on fluid ejection elements 120 of fluid ejection structure 22 to prevent drooling of biosubstances from orifices of fluid ejection elements 120.

Finally, a microtray can include a combination of more than one type of back pressure device. In one embodiment, a single microtray can have both bellows-type and bladder-type back pressure devices mounted on a top surface of the fluid holding structure of that microtray. In addition, multiple back pressure devices can be ganged together with a frame or handled simultaneously by an applicator so that each back pressure device 254, 262, 272 need not be handled separately when mounted on wells 26 of the fluid holding structure 20.

Figure 7A:
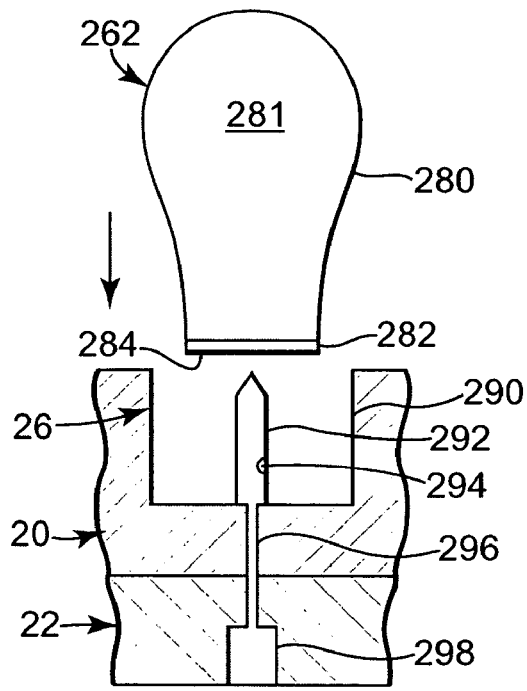
FIG. 7A is sectional view of a back pressure device of a microtray, according to an embodiment of the present invention.
Figure 7B:
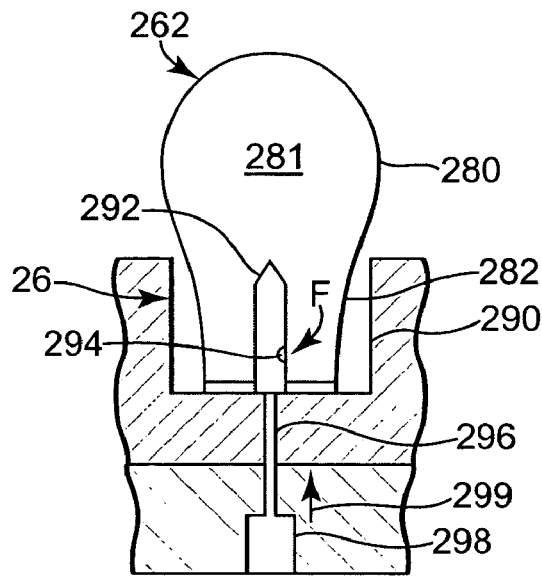
FIG. 7B is a sectional view of a back pressure device of a microtray, according to an embodiment of the present invention.

FIGS. 7A and 7B illustrate one embodiment of applying bladder-type back pressure devices 262 to fluid holding structure 20. As shown in FIG. 7A, bladder-type device 262 comprises inflatable body 280 holding fluid 281 and having a bottom end 282 including a piercable septum 284. Well 26 of fluid holding structure 20 comprises walls 290, with hollow needle 292 extending within well 26 and spaced from walls 290 and having a hole 294 to permit fluid passage therethrough. In use, device 262 is positioned over well 26 and advanced, as represented by directional arrow A, toward needle 292 until needle 292 pierces septum 284. Device 262 is advanced until the position shown in FIG. 7B is achieved, with device 262 set partially within well 26, secured by frictional engagement between septum 284 and a base of needle 292. Biological substances, or other fluids 281 flow from within device 262 through hole 294 of needle 292 and into ejection device 298, via outlet 296. Bladder device 262 provides fluid to ejection device 298 while at the same time, exerting back pressure on ejection device 298, as represented by directional arrow 299 to enable suitable operation of ejection device 298.

Figure 8:
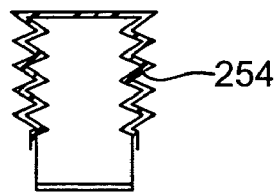
FIG. 8 is a sectional view of a back pressure device of a microtray, according to an embodiment of the present invention.

FIG. 8 illustrates one embodiment of a bellows-type back pressure device 254 that is insertable into or mountable over wells 26 of fluid holding structure 20 for exerting back pressure on a fluid ejection device of fluid ejection structure 22 and/or for filling wells of fluid holding structure 20.

In one embodiment, wells 26 of fluid holding structure 20 are also partially filled with materials, such as beads or foam, in a manner suitable to exert back pressure on fluid ejection devices of fluid ejection structure. These back pressure materials can be used in combination with back pressure devices 254, 262, or 272 or without back pressure devices 254, 262, or 272.

Figure 9:
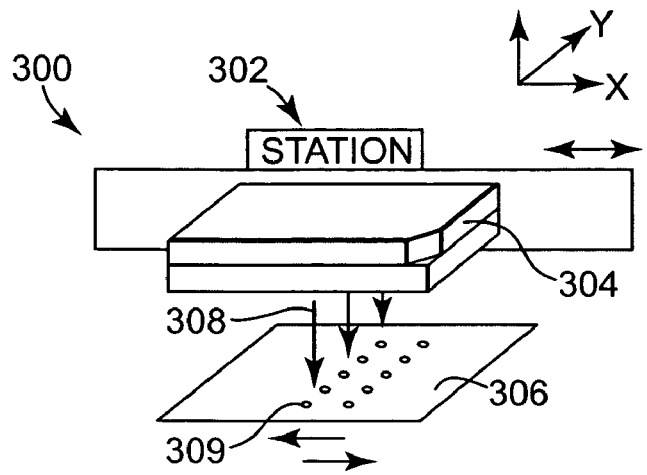
FIG. 9 is a perspective view of a microtray system, according to another embodiment of the present invention.

FIG. 9 illustrates one embodiment of a microtray system 300. Microtray system 300 comprises a fluid handling system including station 302, microtray 304, and target media 306. Microtray 304 deposits drops 308 onto target media 306 as spots 309. In one embodiment, drops are dispensed by microtray 304 onto target media 306 while target media 306 is moved, as represented by directional arrow A, relative to microtray 304 which is held stationary by station 302. In another embodiment, drops are dispensed by microtray 304 onto target media 306 while microtray 304 is moved relative to target media 306, as represented by directional arrow B. Moreover, station 304 can position microtray 304 into a fixed position over target media 306 along any one or more of three axes x, y, z. Finally, as previously described in association with the embodiment of FIG. 2, microtray 304 is releasably secured relative to station 302 so that microtray 304 is removable from station 302 for filling, dispensing, or other functions apart from a location over target media 306.

Figure 10:
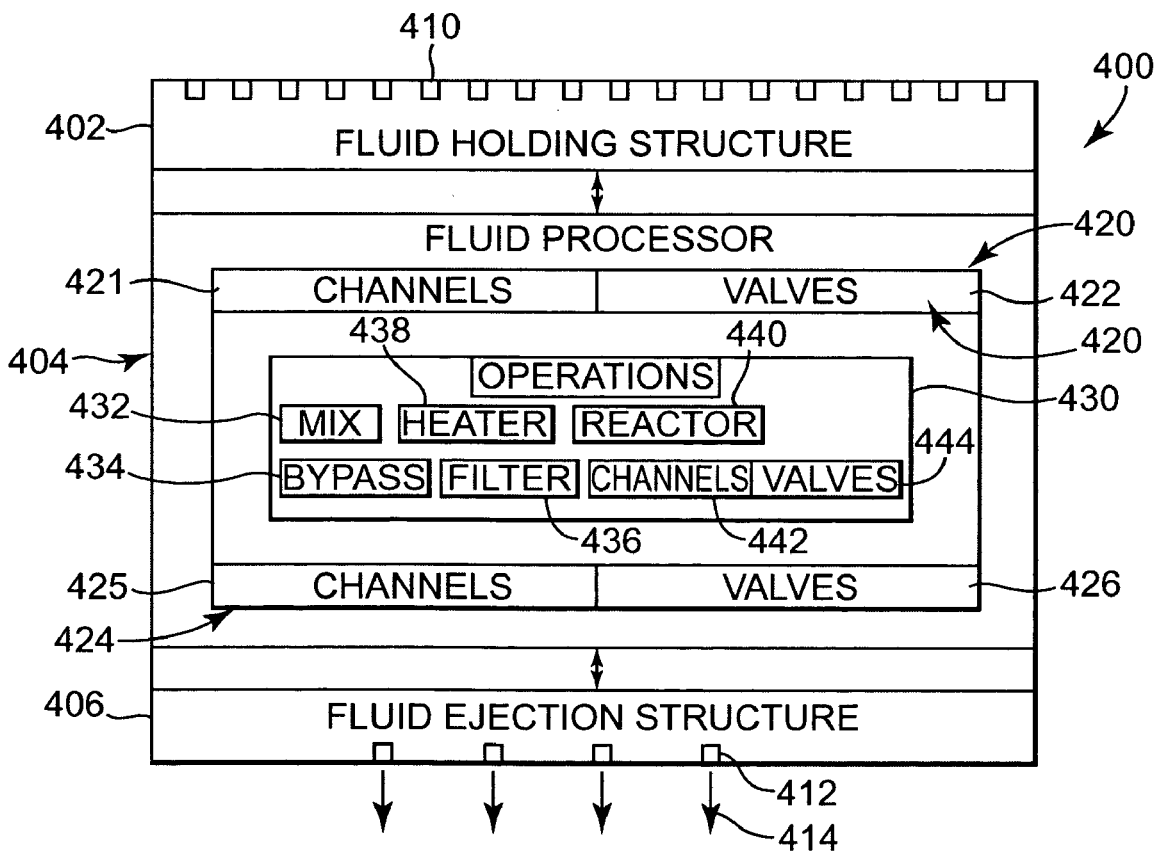
FIG. 10 is a block diagram of a microtray, according to an embodiment of the present invention.

FIG. 10 illustrates one embodiment of a microtray 400. As shown in FIG. 10, microtray 400 comprises fluid holding structure 402 with wells 410, fluid processor 404, and fluid ejection structure 406 with nozzles 412 for ejecting drops 414. Fluid processor 404 is interposed between fluid holding structure 402 and fluid ejection structure 406. Fluid holding structure 402 and fluid ejection structure 406 have substantially the same features and attributes, respectively, as fluid holding structure 20 and fluid ejection structure 22 of embodiment of FIGS. 1-4. Fluid holding structure 402 is in fluid communication with fluid ejection structure 406 via fluid processor 404 to enable dispensing biosubstances from fluid ejection structure 406. In one embodiment, fluid ejection structure 406 comprises a number of nozzles (e.g. 2-20) substantially less than a number of wells of fluid holding structure 402 (e.g., 100-10,000) with biosubstances from these wells communicated to an array of fluid ejection devices (e.g. nozzles) via fluid processor 404. Accordingly, a die forming fluid ejection structure 406 can be much smaller in size (e.g. a footprint) when the biosubstance are routed through fluid processor 404. This smaller die for fluid ejection structure 406 simplifies manufacture, permits greater flexibility in choice of materials in making this die, and enables further miniaturization of microtray 400.

Microtray 400 including fluid processor 404 enables microtray 400 to perform operations on biosubstances within microtray 400 without requiring transport of biosubstances to and from the microtray 400 relative to other microtrays, microplates and/or other external devices. In addition, after these internal operations on biosubstances, fluid ejection structure 406 can dispense the biosubstances without resort to any external devices.

Fluid processor 404 comprises input structure 420 with router 421 and valves 422, operations module 430, and output structure 424 with router 425 and valves 426. Operations module 430 comprises mixer 432, bypass 434, filter 436, heater 438, reactor 440, router 442, and valves 444.

Input structure 420 uses router 421 including one or more channels to enable flow of one or more biological substances from wells in fluid holding structure into fluid processor 404 while valves 422 regulate flow of fluids into various functions, chambers, of operations module 430. Output structure 420 uses router 425, including one or more channels and valves 426, to enable flow of biological substances from fluid processor 404 into fluid ejection structure 406.

Operations module 404 enables performing various operations on biological substances available from wells 410 of fluid holding structure 402, prior to dispensing biosubstances from fluid ejection structure 406. In one embodiment, mixer 432 of fluid processor 404 mixes biological substances together to create new biosubstances, prior to dispensing from fluid ejection structure 406. For example, if each well contains a base nucleotide, mixer 432 can combine different base nucleotides supplied by a plurality of separate wells, to create an oligonucleotide, which then can be dispensed by fluid ejection structure 406.

In one embodiment, heater 438 of fluid processor 404 heats one or more biosubstances prior to dispensing from fluid ejection structure 406. In another embodiment, filter 436 of fluid processor 404 filters a biological substance to separate one or more components or biosubstances from each other, prior to dispensing from fluid ejection structure 406. In one embodiment, bypass 434 of fluid processor 404 enables a biosubstance to flow directly from a fluid holding structure 402 to fluid ejection structure 406 without any other operations (e.g., heating, mixing, etc) being performed on that biosubstance. In one embodiment, reactor 440 of fluid processor 404 enables causing a reaction between two different biosubstances (provided from different wells 410) prior to dispensing from fluid ejection structure 406.

In one embodiment, router 442 (e.g., channels) and valves 444 of fluid processor 404 enable moving biological substances within fluid processor 404 between various functions, such as mixer 432, bypass 434, heater 438, filter 436, reactor 440, etc. As such, biosubstances can be the subject of more than one operation performed by fluid processor 404 before being dispensed by fluid ejection structure 406.

Accordingly, microtray 400 with fluid processor 404 enables performing many operations normally associated different components of a liquid handling systems within microtray 400, independent of and separate from devices external of microtray 400, except for communication with a controller, such as controller 90 of FIG. 2.

Figure 11:
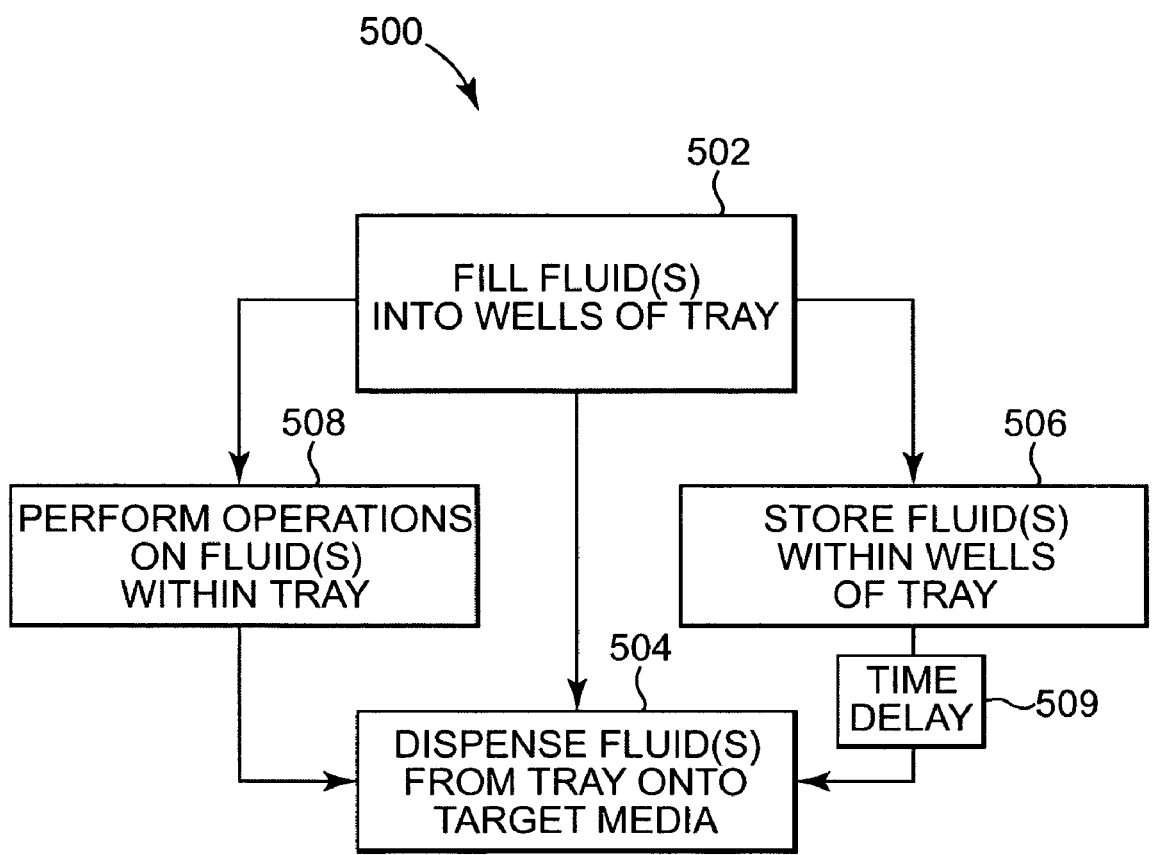
FIG. 11 is a flow diagram of a method of handling substances with a microtray, according to an embodiment of the present invention.

FIG. 11 is a flow diagram illustrating an embodiment of a method of handling biological substances with a microtray. Method 500 can be performed using any one or more of embodiments of FIGS. 1-10, but is not limited to being performed by those components and systems. As shown in FIG. 11, microtray can be used in several ways such as immediately dispensing fluids from wells, or first performing operations on those fluids prior to dispensing, as well as storing the fluids without dispensing or storing the fluids and later dispensing them.

As shown at box of FIG. 11, method 500 comprises placing one or more fluids into wells of the microtray. At box 504, the fluids are dispensed from the microtray onto a target media. At box 506, the fluids are stored within wells of the tray. At box 508, operations are performed on the fluids within the tray prior to dispensing the fluids from the microtray. In one embodiment, shown at box 509, a time delay represents a period of time of storage of a biosubstance before dispensing from a fluid ejection structure.

Finally, any one of microtrays of the embodiments of FIGS. 1-10 are sized and shaped to substantially match the ANSI/SBS standard for microplates to enable their use in conventional liquid handling systems. In another embodiment, any one of the microtrays of the embodiments of FIGS. 1-10 are sized and shaped differently than the ANSI/SBS standard for microplates to enable their use in systems, and/or methods different than conventional liquid handling systems to take advantage of the new functions, features and attributes of embodiments of the present invention. Finally, in other embodiments of microtrays, including a fluid holding structure and a fluid ejection structure, in which larger volumes of biosubstances are dispensed, fluid ejection devices comprises other non-contact, drop-on-demand technologies such as piezoelectric-based of flex-tensional fluid ejection devices capable of dispensing microvolumes of liquids.

Embodiments of the present invention including an active microtray enable more precise and accurate dispensing of biosubstances as well as novel combinations of storage, processing, and/or dispensing of biosubstances not previously available in single liquid handling devices, such as conventional passive microplates. Moreover, these functions are provided in a device that can mimic the size and shape of a conventional microplate, enabling use of this active microtray in some aspects of conventional liquid handling systems. In addition, this increased accuracy and precision in liquid handling will make the use of each chemical and/or biosubstance more cost effective, which is particularly attractive to high volume applications, as high throughput screening in the biotechnology industry.

Although specific embodiments have been illustrated and described herein, it will be appreciated by those of ordinary skill in the art that a variety of alternative and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A microtray for handling biosubstances comprising:
   a fluid holding structure including an array of wells with each well configured to contain at least one biosubstance;
   a fluid ejection structure arranged vertically below, and connected to, the fluid holding structure to define a single unit, the fluid ejection structure including an array of drop-on-demand fluid ejection devices with each fluid ejection device being in fluid communication with at least one of the respective wells and including at least one nozzle, wherein the fluid ejection structure includes circuitry configured to independently activate each respective fluid ejection device and configured to cause, independent of a target media, dispensing of the at least one biosubstance from the at least one nozzle of a respective one of the fluid ejection devices onto the target media;
   an electrically conductive input/output contact element configured to communicate with an external controller; and
   a fluid processor interposed between, and in fluid communication with, the fluid holding structure and the fluid ejection structure, and configured to route the at least one biosubstance from the respective wells to the respective fluid ejection devices, wherein the fluid processor is electrically activated via the input/output contact element and the fluid processor includes at least one of:
   a reactor configured to facilitate a reaction between the at least one biosubstance and at least another biosubstance prior to dispensing from the fluid ejection structure;
   a heater configured to heat the at least one biosubstance prior to dispensing from the fluid ejection structure;
   a mixer configured to mix the at least one biosubstance and at least another biosubstance together prior to dispensing from the fluid ejection structure;
   a filter configured to filter the at least one biosubstance prior to dispensing from the fluid ejection structure; and
   a bypass configured to enable the at least one biosubstance to pass from the fluid holding structure to the fluid ejection structure without interacting with the reactor, the heater, the mixer, and the filter prior to dispensing from the fluid ejection structure.

2. A microtray for handling biosubstances comprising:
   a fluid holding structure including an array of wells with each well configured to contain at least one biosubstance; and
   a fluid ejection structure arranged vertically below, and connected to, the fluid holding structure to define a single unit, the fluid ejection structure including an array of drop-on-demand fluid ejection devices with each fluid ejection device being in fluid communication with at least one of the respective wells and including at least one nozzle, wherein the fluid ejection structure includes circuitry configured to independently activate each respective fluid ejection device and configured to cause, independent of a target media, dispensing of the at least one biosubstance from the at least one nozzle of a respective one of the fluid ejection devices onto the target media, wherein the fluid holding structure and the fluid ejection structure are formed as a single microplate having a length, a width, and a height configured to enable an array of 6144 wells in the fluid holding structure with a pitch between adjacent wells of about 1.125 millimeters, wherein each well of the fluid holding structure uniquely corresponds to, and is in fluid communication with, one of the respective fluid ejection devices to separately dispense volumes of the at least one biosubstance from the at least one nozzle of the respective fluid ejection device onto the target media, wherein the at least one nozzle of each respective fluid ejection device comprises more than one adjacent nozzle configured to eject the same at least one biosubstance through adjacent nozzles to cause duplicate spotting of the same at least one biosubstance on the target media.

3. The microtray of claim 2 wherein at least two of the adjacent nozzles are configured to eject different volume drops of the same at least one biosubstance.

4. A microtray for handling biosubstances comprising:

a fluid holding structure including an array of wells with each well configured to contain at least one biosubstance; and a fluid ejection structure arranged vertically below, and connected to, the fluid holding structure to define a single unit, the fluid ejection structure including an array of drop-on-demand fluid ejection devices with each fluid ejection device being in fluid communication with at least one of the respective wells and including at least one nozzle, wherein the fluid ejection structure includes circuitry configured to independently activate each respective fluid ejection device and configured to cause, independent of a target media, dispensing of the at least one biosubstance from the at least one nozzle of a respective one of the fluid ejection devices onto the target media, wherein each well is sized and shaped to cause a capillary effect on the at least one biosubstance within each well of the fluid holding structure to exert a back pressure on the at least one biosubstance within a corresponding one of the respective fluid ejection devices.

5. A microtray for handling biosubstances comprising:

a fluid holding structure including an array of wells with each well configured to contain at least one biosubstance; and a fluid ejection structure arranged vertically below, and connected to, the fluid holding structure to define a single unit, the fluid ejection structure including an array of drop-on-demand fluid ejection devices with each fluid ejection device being in fluid communication with at least one of the respective wells and including at least one nozzle, wherein the fluid ejection structure includes circuitry configured to independently activate each respective fluid ejection device and configured to cause, independent of a target media, dispensing of the at least one biosubstance from the at least one nozzle of a respective one of the fluid ejection devices onto the target media, wherein the fluid holding structure comprises a plurality of back pressure devices, with each respective back pressure device sealingly arranged relative to each well and configured to maintain back pressure on the at least one biosubstance in each fluid ejection device to prevent drooling from the at least one nozzle of the fluid ejection device.

6. The microtray of claim 5 wherein the back pressure device comprises a sealed bladder having an inflatable body configured to hold the at least one biosubstance and a piercable septum, wherein each well comprises a hollow needle configured to pierce the septum of the bladder to permit flow of the at least one biosubstance from the body of the bladder, through the needle, and out of the well into the respective fluid ejection device in communication with the well.

7. The microtray of claim 5 wherein each back pressure device comprises a sealable bellows-type member configured to hold the at least one biosubstance and to exert back pressure on each fluid ejection device relative to a corresponding well.

8. A microtray for handling biosubstances comprising:

a fluid holding structure including an array of wells with each well configured to contain at least one biosubstance;

a fluid ejection structure arranged vertically below, and connected to, the fluid holding structure to define a single unit, the fluid ejection structure including an array of drop-on-demand fluid ejection devices with each fluid ejection device being in fluid communication with at least one of the respective wells and including at least one nozzle, wherein the fluid ejection structure includes circuitry configured to independently activate each respective fluid ejection device and configured to cause, independent of a target media, dispensing of the at least one biosubstance from the at least one nozzle of a respective one of the fluid ejection devices onto the target media; and an array of hoses with each hose sealingly connected to a respective one of the wells of the fluid holding structure, wherein each hose is configured to direct the at least one biosubstance from an external source into the corresponding respective well, and exert a back pressure on the at least one biosubstance in each corresponding fluid ejection device.

9. A microtray for handling biosubstances comprising:

a fluid holding structure including an array of wells with each well configured to contain at least one biosubstance; and a fluid ejection structure arranged vertically below, and connected to, the fluid holding structure to define a single unit, the fluid ejection structure including an array of drop-on-demand fluid ejection devices with each fluid ejection device being in fluid communication with at least one of the respective wells and including at least one nozzle, wherein the fluid ejection structure includes circuitry configured to independently activate each respective fluid ejection device and configured to cause, independent of a target media, dispensing of the at least one biosubstance from the at least one nozzle of a respective one of the fluid ejection devices onto the target media, wherein each fluid ejection device includes a thermal inkjet drop-generating mechanism configured to eject the at least one biosubstance onto the target media.

10. A microtray for handling biosubstances comprising:

a fluid holding structure including an array of wells with each well configured to contain at least one biosubstance; and a fluid ejection structure arranged vertically below, and connected to, the fluid holding structure to define a single unit, the fluid ejection structure including an array of drop-on-demand fluid ejection devices with each fluid ejection device being in fluid communication with at least one of the respective wells and including at least one nozzle, wherein the fluid ejection structure includes circuitry configured to independently activate each respective fluid ejection device and configured to cause, independent of a target media, dispensing of the at least one biosubstance from the at least one nozzle of a respective one of the fluid ejection devices onto the target media, wherein the fluid ejection structure comprises an electrically conductive input/output contact element in electrical communication with each respective fluid ejection device and configured to communicate with an external controller.

11. The microtray of claim 10 and further comprising a station configured to position the microtray relative to the target media for dispensing the at least one biosubstance, and the station comprising an electrically conductive input/output contact element configured for electrical communication with the input/output contact element of the microtray for electrical actuation of the fluid ejection device.

* * * * *

UNITED STATES PATENT AND TRADEMARK OFFICE
CERTIFICATE OF CORRECTION

PATENT NO.         : 7,651,665 B2                                           Page 1 of 1
APPLICATION NO.    : 10/935029
DATED              : January 26, 2010
INVENTOR(S)        : Jose M. Gonzalez et al.

It is certified that error appears in the above-identified patent and that said Letters Patent is hereby corrected as shown below:

In column 13, line 24, delete "piercable" and insert -- pierceable --, therefor.

In column 18, lines 10-11, in Claim 6, delete "piercable" and insert -- pierceable --, therefor.

Signed and Sealed this

Thirteenth Day of July, 2010

David J. Kappos
*Director of the United States Patent and Trademark Office*